United States Patent
Jeon et al.

(10) Patent No.: US 9,434,907 B2
(45) Date of Patent: Sep. 6, 2016

(54) FRAGRANCE COMPOSITION HAVING GOOD SLEEP-INDUCING EFFECT

(75) Inventors: Byeong Bae Jeon, Yongin-si (KR); Hyung Jye Seo, Yongin-si (KR); Yeon Ju Hong, Yongin-si (KR); Ji Young Choi, Yongin-si (KR); Mi Jung Kwon, Gangwon-du (KR)

(73) Assignee: AMOREPACIFIC CORPORATION, Seoul (KR)

( * ) Notice: Subject to any disclaimer, the term of this patent is extended or adjusted under 35 U.S.C. 154(b) by 129 days.

(21) Appl. No.: 13/319,787

(22) PCT Filed: Sep. 28, 2009

(86) PCT No.: PCT/KR2009/005523
§ 371 (c)(1),
(2), (4) Date: Nov. 10, 2011

(87) PCT Pub. No.: WO2010/134670
PCT Pub. Date: Nov. 25, 2010

(65) Prior Publication Data
US 2012/0052139 A1     Mar. 1, 2012

(30) Foreign Application Priority Data

May 19, 2009    (KR) ........................ 10-2009-0043726

(51) Int. Cl.
*A61K 36/738*     (2006.01)
*C11B 9/00*     (2006.01)

(52) U.S. Cl.
CPC ........................................ *C11B 9/00* (2013.01)

(58) Field of Classification Search
None
See application file for complete search history.

(56) References Cited

U.S. PATENT DOCUMENTS

| | | | |
|---|---|---|---|
| 3,963,648 A * | 6/1976 | Jones et al. | ..................... 512/25 |
| 4,659,509 A | 4/1987 | Asakawa | |
| 2003/0064120 A1 | 4/2003 | Librizzi et al. | |
| 2007/0207220 A1 | 9/2007 | Luedtke et al. | |

FOREIGN PATENT DOCUMENTS

| | | |
|---|---|---|
| CN | 1709957 A | 12/2005 |
| CN | 1911120 A | 2/2007 |
| CN | 101199622 A | 6/2008 |
| JP | 2000-355545 | 12/2000 |
| WO | WO 2005/062730 A2 | 7/2005 |

OTHER PUBLICATIONS

From IDS, Abstract JP 2000355545 A.*
English translation of Office Action and Office Action in CN200980158859.2 dated Nov. 1, 2012.
Examination Report dated Sep. 18, 2012 in New Zealand SN 596130.
International Search Report for PCT/KR2009/005523 mailed Apr. 30, 2010.
Written Opinion of the International Searching Authority mailed Apr. 30, 2010.
Kimori, T. et al., The sleep-enhancing effect of valerian inhalation and sleep-shortening effect of lemon inhalation, Chemical Senses, 2006, 31(8), pp. 731-737.
Examination Report in New Zealand Patent Application 596130 issued Sep. 18, 2012.
Komori et al, "The Sleep-Enhancing Effect of Valerian Inhalation and Sleep-Shortening Effect of Lemon Inhalation", Chemical Senses, Issue 31, pp. 731-737, Dec. 2006.
Second Notification of Office Action and English translation in Chinese Application No. 200980158859.2 issued Apr. 11, 2013.

* cited by examiner

*Primary Examiner* — Terry A. McKelvey
*Assistant Examiner* — Catheryne Chen
(74) *Attorney, Agent, or Firm* — Nixon & Vanderhye P.C.

(57) ABSTRACT

Disclosed herein is a fragrance composition which contains natural oils, including rose oil and sandalwood oil, and has a good sleep-inducing effect. More specifically, disclosed is a fragrance composition which contains rose oil, sandalwood oil, neroli oil and ylang-ylang oil and creates a comfortable sleeping environment using the good sleep-inducing effects of the natural fragrance oils.

3 Claims, 2 Drawing Sheets

FRAGRANCE COMPOSITION HAVING GOOD SLEEP-INDUCING EFFECT

This application is the U.S. national phase of International Application No. PCT/KR2009/005523 filed 28 Sep. 2009 which designated the U.S. and claims priority to KR 10-2009-0043726 filed 19 May 2009, the entire contents of each of which are hereby incorporated by reference.

TECHNICAL FIELD

The present invention relates to a fragrance composition which contains natural oils, including rose oil and sandalwood oil, and has a good sleep-inducing effect. More particularly, the present invention relates to a fragrance composition which contains rose oil, sandalwood oil, neroli oil and ylang-ylang oil and creates a comfortable sleeping environment using the good sleep-inducing effects of the natural fragrance oils.

BACKGROUND ART

Improving the quality of life, including environment and health, is one of the greatest challenges facing mankind in the 21 century. In view of this, high-preference products which provide an environment capable of enhancing the quality of healthy life for people and is required for a comfortable and easy life should be developed. Namely, human physical and emotional responses which change according to the surrounding environmental conditions need to be measured for application to the development of products.

For this purpose, emotional engineering studies focused on determining the relationship between products and the emotional and physiological state of people by observing the emotional and physiological responses of people to the products are currently being actively conducted in Korea and other countries. Such emotion-related studies have been conducted mainly on the sight and hearing senses, but are still insufficient on the sense of smell (fragrance).

The sense of smell is a chemical sense, unlike other senses (sight and hearing senses), and thus is difficult to study, because precise stimulus control is required and, in addition, nerve transmission to the brain simultaneously with the presentation of smell stimulus, the evaluation of mental emotion, and physiological changes (central and autonomic nervous systems) occur.

People frequently experience odors, stimulating the sense of smell, in their daily life, and the emotion of people is influenced by a variety of odors, including fragrant odors and unpleasant odors. Recently, studies on the effects of the odors of plants (such as garlic) and offensive odors (such as ammonia) on physiological action in addition to studies either on the effects of green shower or on the effects of pheromones on the sexual behavior of animals have been conducted.

The impulse of smell is transmitted to the limbic system through nasal olfactory cells to add the emotional factors of the olfactory sense, thus inducing emotional and physiological changes, such as pleasure, sickening, awakening or sleepy feelings. This phenomenon explains that when a person sniffs perfume, a strong mood is created, and when a person smells an unpleasant odor, defensive reflexes such as sneezing occur, and when a person smells an odor such as ammonia, the breath is temporarily stopped. As described above, the sense of smell plays a great role in the maintenance of human life and the discrimination of odors.

Sleep is an important physiological function in animals with developed brains and is an essential behavior for survival. All organisms on the earth live in an environment in which day and night alternate. Being synchronized to the diurnal cycle and repeating the rhythm of activity and rest according to this diurnal cycle are the most fundamental survival strategy of organisms. Therefore, all organisms have circadian biological clocks in the body and are entrained to the environmental cycle.

Lack of sleep causes a sleepy feeling or temper or reduces vital energy, leading to the loss of the quality of life. In some cases, it may cause seriously impair life quality. Sleep is a function for preventing such states from occurring, and for this reason, it is very important to sleep well.

DISCLOSURE OF INVENTION

Technical Problem

Accordingly, the present inventors have conducted studies to verify whether or not essential oils have a good sleep-inducing effect. The present inventors have conducted studies to prepare a fragrance composition having a good sleep-inducing effect only using natural fragrances and, as a result, have carried out latency sleep analysis, slow-wave sleep analysis, sleep efficiency analysis and body movement analysis for a fragrance composition containing rose oil, sandalwood oil, neroli oil and ylang-ylang oil.

As a result, the present inventors have found that the fragrance composition suggested in the present invention shows an excellent sleep-inducing effect for the human body together with high preference, thereby completing the present invention.

Therefore, it is an object of the present invention to provide a fragrance composition having a good sleep-inducing effect.

Solution to Problem

To achieve the above object, the present invention provides a fragrance composition containing rose oil, sandalwood oil, neroli oil and ylang-ylang oil.

Advantageous Effects of Invention

The present invention provides a fragrance composition containing rose oil, sandalwood oil, neroli oil and ylang-ylang oil. When the fragrance composition is used in cosmetic products, it can show a good sleep-inducing effect of creating a comfortable sleeping environment for users.

BEST MODE FOR CARRYING OUT THE INVENTION

Figure 1:
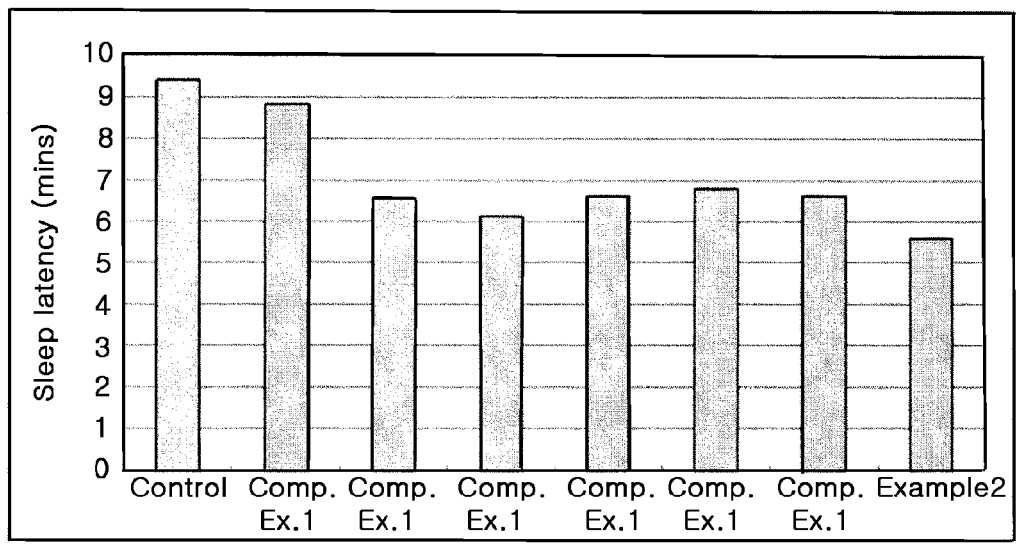
FIG. 1 is a graphic diagram showing the results obtained by measuring sleep latency for each of Examples, a control and Comparative Examples 1 to 6.

The fragrance composition according to the present invention contains, based on the total weight of the composition, 40-60 wt % of rose oil, 10-30 wt % of sandalwood oil, 10-20 wt % of neroli oil and 1-10 wt % of ylang-ylang oil. If the contents of the oils in the fragrance composition deviate from these ranges, the desired sleep-inducing effect cannot be obtained.

The fragrance composition according to the present invention can be added to skin external preparations such as perfumes or cosmetic products, and the amount of composition added can be suitably selected by a person of ordinary skill in the art so as to achieve the desired effect. The skin external preparations to the fragrance composition can be added are not specifically limited and the fragrance composition can be added to any preparation known in the art. Examples of the preparations include packs, ointments, lotions, solubilized phases, suspensions, emulsions, creams, gels, sprays, cataplasms, plasters, patches, and external liquid preparations.

Hereinafter, the present invention will be described in further detail.

Rose oil which is used in the present invention is a yellow liquid obtained by distilling natural rose flowers with steam and has effects on nervous tension relief, sedation and depression alleviation.

Sandalwood oil which is used in the present invention is a light-yellow viscous liquid obtained by cutting down a sandalwood tree, removing branches and leaves from the cut-down tree, chopping the tree into small pieces and drying the chopped tree. It is a natural fragrance having antidepressant, aphrodisiac, astringent and sedative effects.

Neroli oil which is used in the present invention is a yellow liquid obtained by distilling bitter orange flowers with steam and has antidepressant, disinfectant, anti-convulsant and aphrodisiac effects.

Ylang-ylang oil which is used in the present invention is a liquid obtained by distilling natural ylang-ylang oils with steam and has anti-depressant, sedative, tonic, aphrodisiac and disinfectant effects.

Meanwhile, in the present invention, sleep latency analysis, slow-wave sleep analysis, sleep efficiency analysis and body movement analysis were carried out to verify the effect of the fragrance composition.

As can be seen from the results of test examples below, the use of the natural fragrances of the present invention shortened sleep latency, increased slow-wave sleep, increased sleep efficiency and reduced the number of body movements.

Accordingly, the present invention can provide a fragrance composition containing the above natural fragrances as active ingredients.

MODE FOR THE INVENTION

Hereinafter, the present invention will be described in further detail with reference to examples and test examples. It is to be understood, however, that these examples are for illustrative purposes only and are not to be construed to limit the scope of the present invention.

Example 1

Fragrance Composition Having Good Sleep-Inducing Effect

A fragrance composition was prepared using a conventional method according to the composition shown in Table 1 below, and the good sleep-inducing effect of the fragrance composition was tested.

TABLE 1

Mixing ratios of fragrance oils in composition having good sleep-inducing effect (unit: wt %)

| Ingredients | Example 1 (wt %) |
|---|---|
| Rose oil | 40 |
| Sandalwood oil | 30 |
| Neroli oil | 20 |
| Ylang-ylang oil | 10 |
| Total | 100 |

Test Example 1

Measurement of Good Sleep-Inducing Effect of Fragrance Composition

In order to objectively evaluate the good sleep-inducing effect of the fragrance composition according to the present invention, the fragrance composition shown in Table 1 above was used to carry out sleep latency analysis, slow-wave sleep analysis, sleep efficiency analysis and body movement analysis. Specific analysis methods were as follows:

1. Test Subjects

Experimental subjects were ten women in their 20s to 30s, who were healthy, were not being administered with a drug and were not odor-blind. The subjects were instructed to refrain from immoderate exercise or excessive drinking and eating at the day before the experiment and to abstain from smoking and the ingestion of beverages, drugs and gums, which would influence the central nervous system and the sense of smell, at the day of the experiment. The experiment was carried out in consideration of the menstrual cycles of the subjects, because it was reported that there is a relationship between a change in the sense of fragrance and the menstrual cycle and feeling of women in experiments employing women as test subjects.

2. Experimental Samples

Samples used in this test example were as follows: a sleeping pack (Example 2) containing the fragrance composition of Example 1; a general fragrance-less pack (Comparative Example 2); a general pack containing lavender oil known to have a good sleep-inducing effect (Comparative Example 2); a general pack containing rose oil (Comparative Example 3); a general pack containing sandalwood oil (Comparative Example 4); a general pack containing neroli oil (Comparative Example 5); a general pack containing ylang-ylang oil (Comparative Example 6); and a control in which no pack was used. The experiment was carried out in a total of 8 kinds of conditions consisting of the condition in which no pack was used and the conditions in which each of 7 kinds of packs was used. In 7 kinds of conditions excluding the condition in which no pack was used, each of the packs was applied directly to the face after facial washing.

After the application of the pack, the subjects were instructed to sleep. During sleeping, polysomnography was carried out by measuring EEG, EOG, chin EMG, and ECG.

The cosmetic pack compositions used in Example 2 and Comparative Examples 1 to 6 are shown in Table 2 below.

TABLE 2

Cosmetic pack compositions

| Ingredients | Example 2 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|
| 1. Purified Water | to 100 | to 100 | to 100 | to 100 | to 100 | to 100 | to 100 |
| 2. Cyclopentasiloxane | 6.30 | 6.30 | 6.30 | 6.30 | 6.30 | 6.30 | 6.30 |
| 3. Butylene Glycol | 6.00 | 6.00 | 6.00 | 6.00 | 6.00 | 6.00 | 6.00 |
| 4. Glycerin | 2.10 | 2.10 | 2.10 | 2.10 | 2.10 | 2.10 | 2.10 |
| 5. Trehalose | 2.00 | 2.00 | 2.00 | 2.00 | 2.00 | 2.00 | 2.00 |
| 6. Dimethicone/Vinyl Dimethicone Crosspolymer | 0.10 | 0.10 | 0.10 | 0.10 | 0.10 | 0.10 | 0.10 |
| 7. Dimethiconol | 0.20 | 0.20 | 0.20 | 0.20 | 0.20 | 0.20 | 0.20 |
| 8. Disodium EDTA | 0.02 | 0.02 | 0.02 | 0.02 | 0.02 | 0.02 | 0.02 |
| 9. Ammonium Acryloyldimethyltaurate/ VP Copolymer | 0.50 | 0.50 | 0.50 | 0.50 | 0.50 | 0.50 | 0.50 |
| 10. carbomer | 0.20 | 0.20 | 0.20 | 0.20 | 0.20 | 0.20 | 0.20 |
| 11. Triethanolamine | 0.40 | 0.40 | 0.40 | 0.40 | 0.40 | 0.40 | 0.40 |
| 12. Polysorbate 20 | 0.60 | 0.60 | 0.60 | 0.60 | 0.60 | 0.60 | 0.60 |
| 13. Methyl paraben | 0.20 | 0.20 | 0.20 | 0.20 | 0.20 | 0.20 | 0.20 |
| 14. Chlorphenesin | 0.30 | 0.30 | 0.30 | 0.30 | 0.30 | 0.30 | 0.30 |
| 15. Fragrance (Example 1) | 0.10 | — | — | — | — | — | — |
| 16. Fragrance (Lavender oil) | — | — | 0.10 | — | — | — | — |
| 17. Fragrance (Rose oil) | — | — | — | 0.10 | — | — | — |
| 18. Fragrance (Sandalwood oil) | — | — | — | — | 0.10 | — | — |
| 19. Fragrance (Neroli oil) | — | — | — | — | — | 0.10 | — |
| 20. Fragrance (Ylang-ylang oil) | — | — | — | — | — | — | 0.10 |

3. Experimental Conditions

The experiment was carried out in a sleep laboratory room (4.8 m×3 m×2.4 m) constructed by the present inventors. In order to eliminate the influence of external environment during the experiment, soundproofing equipment was provided in the sleep laboratory room. The sleep laboratory room was kept at a constant temperature and humidity of 24? and 40%.

4. Measurement Method

As physiological signals during sleep, EEG, EOG, chin EMG, and ECG were measured using a polysomnography system. Also, body movements were measured using Acti-heart (Mini Mitter Company, Inc.).

5. Experimental Procedure

The experiment was carried out in a total of 8 kinds of conditions consisting of the condition in which no pack was used and the conditions in which each of 7 kinds of packs was used. In the experiment, each of the packs was applied directly to the face after facial washing. After the application of the pack, the subjects were instructed to sleep. In order to eliminate the effect of order on sleep, the samples were randomly applied to each of the subjects. Before carrying out the experiment, the subjects were instructed to sleep 1-2 times in the sleep laboratory room in order to adapt to the sleep laboratory room. The sleep time was 2 hours, and the subjects were instructed to sleep at the same time.

6. Analytical Method

During sleep of the subjects, physiological signals were used using a polysomnography system, and sleep stages were analyzed using the measured signals. The sleep stages were classified according to the internationally accepted criteria of Rechtschaffen and Kales (1968).

Using the classified sleep stages, sleep latency, slow-wave sleep and sleep efficiency were compared between the samples, and the number of body movements was compared between the samples. Statistical analysis was carried out using SPSS program by ANOVA, t-test and Turkey s test.

7. Experimental Results 7.1. Measurement of Sleep Latency

Sleep latency is the time between going to bed and falling asleep. For each of the samples, the time (minutes) needed to fall asleep was evaluated, and the evaluation results are shown in FIG. 1.

As can be seen from the results in FIG. 1, the average of the sleep latencies was the longest in the case of the control group in which no pack was used, and the time to fall asleep was the shortest in the case of Example 2 containing the fragrance oils.

7.2. Measurement of Slow-Wave Sleep

Slow-wave sleep refers to sleep stages 3 and 4 and is quiet sleep. The ratio of slow-wave sleep to total sleep time was evaluated for each of the samples, and the evaluation results are shown in FIG. 2.

Figure 2:
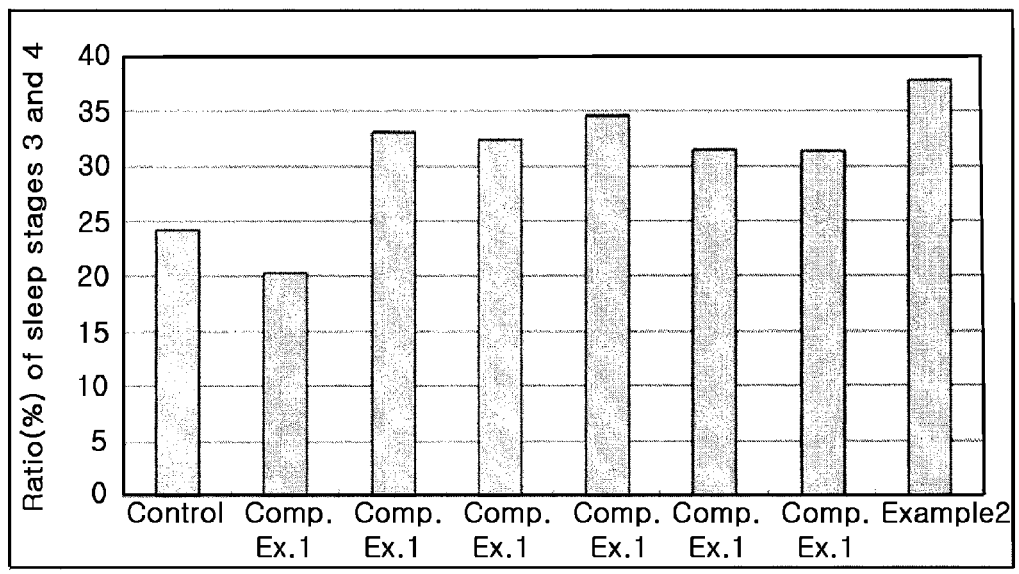
FIG. 2 is a graphic diagram showing the results obtained by measuring slow-wave sleep for each of Examples, a control and Comparative Examples 1 to 6.

As can be seen from the results in FIG. 2, the average slow-wave sleep was the lowest in the case of Comparative Example 1 and the highest in the case of Example 2 containing the fragrance oils.

7.3. Measurement of Sleep Efficiency

Sleep efficiency is the ratio of total sleep time to time spent in bed. It was evaluated for each of the samples, and the evaluation results are shown in FIG. 3.

Figure 3:
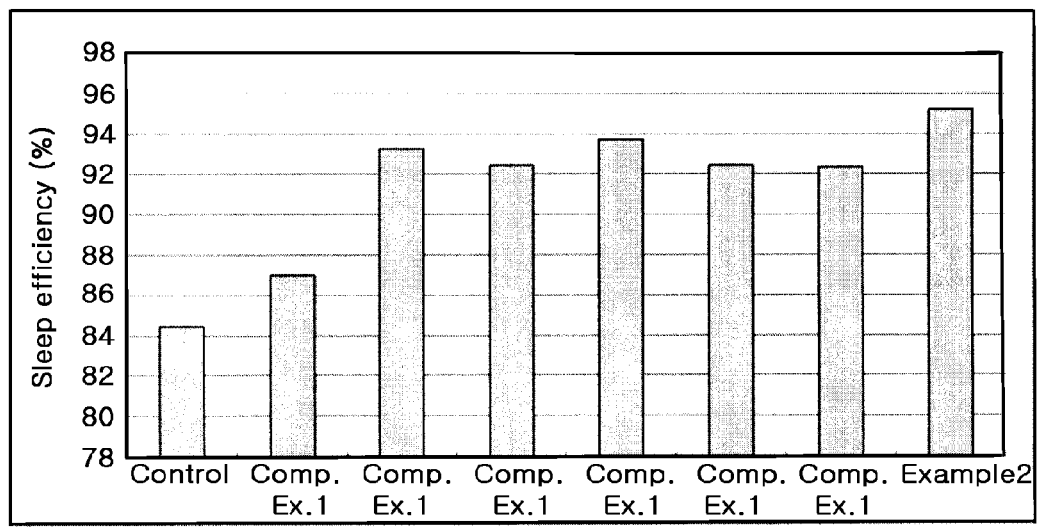
FIG. 3 is a graphic diagram showing the results obtained by measuring sleep efficiency for each of Examples, a control and Comparative Examples 1 to 6.

As can be seen from the results in FIG. 3, the average sleep efficiency was the lowest in the control group and the highest in the case of Example 2 containing the fragrance oils.

7.4. Measurement of Body Movement Frequency

Body movement frequency is the number of movements of each subject during sleep. It was measured using a body movement meter, and the measurement results are shown in FIG. 4.

Figure 4:
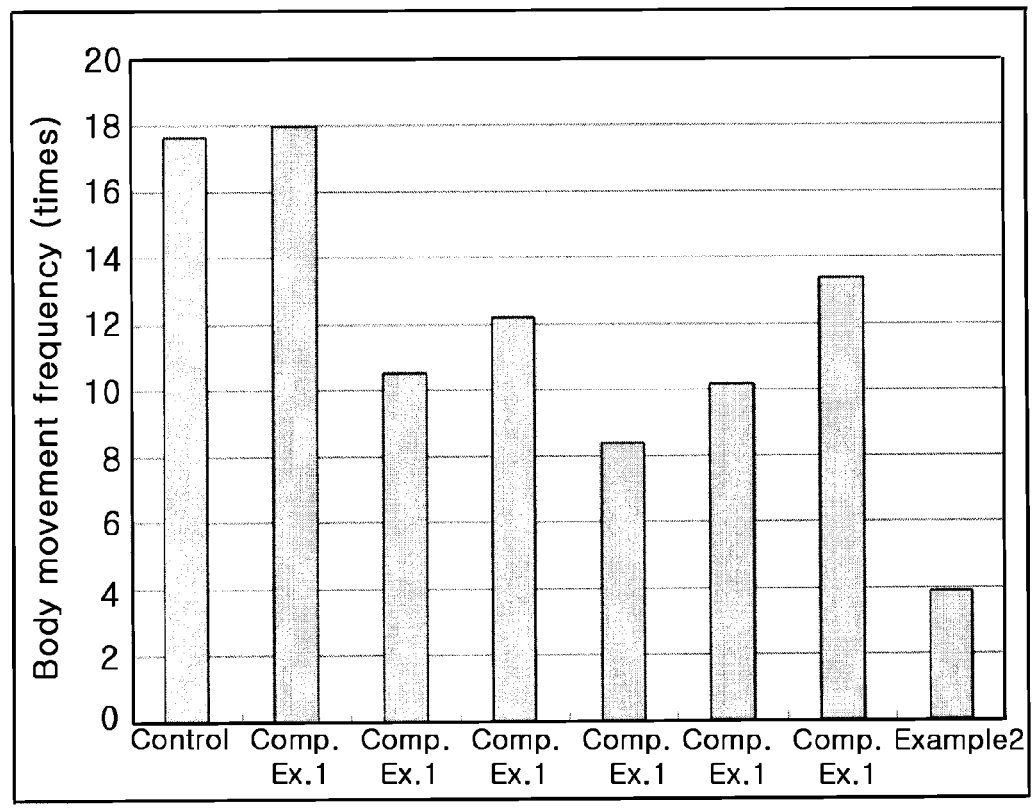
FIG. 4 is a graphic diagram showing the results obtained by measuring body movement frequency for each of Examples, a control and Comparative Examples 1 to 6.

As can be seen from the results in FIG. 4, in the condition of Comparative Example 1, about 18 movements were shown during the experimental time, and this movement number was the highest among the eight conditions. Particularly, in the condition of Example 2 containing the fragrance oils, the number of movements during sleep was significantly reduced compared to the other conditions.

The invention claimed is:

1. A fragrance composition which contains, based on the total weight of the composition, 40-60 wt % of rose oil, 10-30 wt % of sandalwood oil, 10-20 wt % of neroli oil and 1-10 wt % of ylang-ylang oil.

2. A fragrance composition of claim 1, wherein the fragrance composition has a good sleep-inducing effect.

3. A method of inducing sleep as evidenced by at least one of shortened sleep latency, increased slow-wave sleep, increased sleep efficiency and/or reduced the number of body movements, comprising exposing to a subject in need thereof a fragrance composition containing, based on the total weight of the composition, 40-60 wt % rose oil, 10-30 wt % sandalwood oil, 10-20 wt % neroli oil and 1-10 wt % ylang-ylang oil.

* * * * *